(12) United States Patent
Ginn et al.

(10) Patent No.: US 8,083,768 B2
(45) Date of Patent: Dec. 27, 2011

(54) VASCULAR PLUG HAVING COMPOSITE CONSTRUCTION

(75) Inventors: Richard S. Ginn, Gilroy, CA (US); Thomas J Palermo, San Jose, CA (US); Phil Olsen, Cupertino, CA (US); Tellis Hartridge, Santa Clara, CA (US); Adam Shively, San Carlos, CA (US)

(73) Assignee: Ensure Medical, Inc., Sunnyvale, CA (US)

( * ) Notice: Subject to any disclaimer, the term of this patent is extended or adjusted under 35 U.S.C. 154(b) by 1331 days.

(21) Appl. No.: 11/038,995

(22) Filed: Jan. 19, 2005

(65) Prior Publication Data

US 2005/0267528 A1 Dec. 1, 2005

Related U.S. Application Data

(63) Continuation-in-part of application No. 10/142,735, filed on May 10, 2002, now Pat. No. 6,896,692, which is a continuation-in-part of application No. 09/866,548, filed on May 25, 2001, now Pat. No. 6,663,655, which is a continuation-in-part of application No. 09/738,431, filed on Dec. 14, 2000, now Pat. No. 6,846,319.

(51) Int. Cl.
*A61B 17/04* (2006.01)
*A61F 13/00* (2006.01)

(52) U.S. Cl. ........................................ 606/232; 424/422

(58) Field of Classification Search .................. 606/232, 606/151; 424/422–425, 443, 444; 623/23.75, 623/23.76; 128/830–833; 435/402; 530/356
See application file for complete search history.

(56) References Cited

U.S. PATENT DOCUMENTS 287,046 A 10/1883 Norton
(Continued)

FOREIGN PATENT DOCUMENTS

DE 3922203 10/1990
(Continued)

OTHER PUBLICATIONS

E.H. Cassinelli, M.D., et al., Biochemistry of Intervertebral Disk Degeneration and the Potential for Gene Therapy Applications, SpineLine, The Clinical & News Magazine for Spine Care Professionals, vol. 11, Issue 1, Jan.-Feb. 2001.
K. Nishimura, M.D., et al., "Percutaneous Reinsertion of the Nucleus Pulposus, An Experimental Study", SPINE vol. 23, No. 14, pp. 1531-1539, 1998.
Maurice Hiles, "New Specialty Polymer Products Through Interpenetrating Polymer Network (IPN) Technology—The Development of an Interpenetrating Polymer Network to Contain Mechanically Induced Vibration," Oct. 20-21, 1986, Colony Square Hotel, Atlanta, GA.
Zoltan G. Turi, M.D., "Overview of Vascular Closure", Endovascular Today, Closure Update 2008, pp. 28-37.

*Primary Examiner* — Julian Woo
(74) *Attorney, Agent, or Firm* — Dergosits & Noah LLP; Todd A. Noah (57) ABSTRACT

This invention relates to apparatus and methods for use in sealing a vascular puncture site, particularly sites of punctures that are the result of catheterization or other interventional procedures. In several of the preferred embodiments, the sealing device includes a sealing member and a tether. The sealing member generally performs the function of occupying a space in an incision, puncture, or other wound and sealing the space in the incision, puncture, or wound that it occupies, to prevent further blood flow. The tether is typically attached in some manner to the sealing member, and provides the user with the ability to withdraw the sealing member if necessary. In a particularly preferred form, the sealing device further includes a restraining member associated with the sealing member. The restraining member provides the ability to more securely restrain the sealing member to prevent it from migrating from the deployment location within a tissue tract. The restraining member may also provide an additional capability of manipulating the sealing member after deployment.

17 Claims, 10 Drawing Sheets

U.S. PATENT DOCUMENTS

| | | |
|---|---|---|
| 2,696,887 A | 1/1961 | Darmstadt et al. |
| 3,015,403 A | 1/1962 | Fuller |
| 3,678,158 A | 7/1972 | Sussman |
| 3,683,655 A | 8/1972 | White et al. |
| 3,757,783 A | 9/1973 | Alley |
| 3,875,595 A | 4/1975 | Froning |
| 3,941,127 A | 3/1976 | Froning |
| 3,944,114 A | 3/1976 | Coppens |
| 3,952,377 A | 4/1976 | Morell |
| 3,964,480 A | 6/1976 | Froning |
| 4,269,174 A | 5/1981 | Adair |
| 4,301,802 A | 11/1981 | Poler |
| 4,439,423 A | 3/1984 | Smith |
| 4,447,915 A | 5/1984 | Weber |
| 4,509,233 A | 4/1985 | Shaw |
| 4,525,157 A | 6/1985 | Vaillancourt |
| 4,586,502 A | 5/1986 | Bedi et al. |
| 4,638,799 A | 1/1987 | Moore |
| 4,719,108 A | 1/1988 | Smith |
| 4,738,658 A | 4/1988 | Magro et al. |
| 4,741,330 A | 5/1988 | Hayhurst |
| 4,741,336 A | 5/1988 | Failla et al. |
| 4,744,364 A | 5/1988 | Kensey |
| 4,772,287 A | 9/1988 | Ray et al. |
| 4,802,478 A | 2/1989 | Powell |
| 4,837,285 A * | 6/1989 | Berg et al. .................. 530/356 |
| 4,852,568 A | 8/1989 | Kensey |
| 4,863,477 A | 9/1989 | Monson |
| 4,878,893 A | 11/1989 | Chin |
| 4,878,915 A | 11/1989 | Brantigan |
| 4,890,612 A | 1/1990 | Kensey |
| 4,904,260 A | 2/1990 | Ray et al. |
| 4,968,298 A | 11/1990 | Michelson |
| 4,998,934 A | 3/1991 | Bernstein |
| 5,002,557 A | 3/1991 | Hasson |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,032,125 A | 7/1991 | Durham et al. |
| 5,061,274 A | 10/1991 | Kensey |
| 5,108,420 A | 4/1992 | Marks |
| 5,114,032 A | 5/1992 | Laidlaw |
| 5,123,926 A | 6/1992 | Pisharodi |
| 5,190,050 A | 3/1993 | Nitzsche |
| 5,192,301 A | 3/1993 | Kamiya et al. |
| 5,192,302 A | 3/1993 | Kensey et al. |
| 5,222,974 A | 6/1993 | Kensey et al. |
| 5,232,451 A | 8/1993 | Freitas et al. |
| 5,258,042 A | 11/1993 | Mehta |
| 5,269,321 A * | 12/1993 | MacDonald et al. ......... 128/830 |
| 5,275,616 A | 1/1994 | Fowler |
| 5,290,310 A | 3/1994 | Makower et al. |
| 5,292,332 A | 3/1994 | Lee |
| 5,304,184 A | 4/1994 | Hathaway et al. |
| 5,306,234 A | 4/1994 | Johnson |
| 5,306,254 A | 4/1994 | Nash et al. |
| 5,312,435 A | 5/1994 | Nash et al. |
| 5,318,525 A | 6/1994 | West et al. |
| 5,320,639 A | 6/1994 | Rudnick |
| 5,334,216 A | 8/1994 | Vidal et al. |
| 5,334,217 A | 8/1994 | Das |
| 5,342,393 A | 8/1994 | Stack |
| 5,383,852 A | 1/1995 | Stevens-Wright |
| 5,383,905 A | 1/1995 | Golds et al. |
| RE34,866 E | 2/1995 | Kensey et al. |
| 5,411,520 A | 5/1995 | Nash et al. |
| 5,425,757 A | 6/1995 | Tiefenbrun et al. |
| 5,431,639 A | 7/1995 | Shaw |
| 5,443,481 A | 8/1995 | Lee |
| 5,486,195 A | 1/1996 | Myers et al. |
| 5,492,763 A | 2/1996 | Barry et al. |
| 5,507,744 A | 4/1996 | Tay et al. |
| 5,512,474 A * | 4/1996 | Clapper et al. ................ 435/402 |
| 5,522,840 A | 6/1996 | Krajicek |
| 5,531,759 A | 7/1996 | Kensey et al. |
| 5,549,633 A | 8/1996 | Evans et al. |
| 5,549,679 A | 8/1996 | Kuslich |
| 5,554,162 A | 9/1996 | Delange |
| 5,562,736 A | 10/1996 | Ray et al. |
| 5,571,181 A | 11/1996 | Li |
| 5,571,189 A | 11/1996 | Kuslich |
| 5,573,994 A | 11/1996 | Kabra et al. |
| 5,588,424 A | 12/1996 | Insler et al. |
| 5,588,992 A | 12/1996 | Scott et al. |
| 5,591,206 A | 1/1997 | Moufarrege |
| 5,601,556 A | 2/1997 | Pisharodi |
| 5,645,565 A | 7/1997 | Rudd et al. |
| 5,674,296 A | 10/1997 | Bryan et al. |
| 5,676,689 A | 10/1997 | Kensey et al. |
| 5,681,334 A | 10/1997 | Evans et al. |
| 5,690,674 A | 11/1997 | Diaz |
| 5,702,421 A | 12/1997 | Schneidt |
| 5,707,352 A | 1/1998 | Sekins et al. |
| 5,713,911 A | 2/1998 | Racenet |
| 5,720,748 A | 2/1998 | Kuslich et al. |
| 5,725,554 A | 3/1998 | Simon et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,146 A | 3/1998 | Burkett et al. |
| 5,741,429 A | 4/1998 | Donadio, III et al. |
| 5,800,549 A | 9/1998 | Bao et al. |
| 5,800,550 A | 9/1998 | Sertich |
| 5,810,810 A | 9/1998 | Tay et al. |
| 5,814,062 A | 9/1998 | Sepetka et al. |
| 5,830,125 A | 11/1998 | Scribner et al. |
| 5,830,171 A | 11/1998 | Wallace |
| 5,843,124 A | 12/1998 | Hammerslag |
| 5,853,422 A | 12/1998 | Huebsch et al. |
| 5,855,601 A | 1/1999 | Bessler et al. |
| 5,857,999 A | 1/1999 | Quick et al. |
| 5,861,004 A | 1/1999 | Kensey et al. |
| 5,865,846 A | 2/1999 | Bryan et al. |
| 5,871,474 A | 2/1999 | Hermann et al. |
| 5,871,501 A | 2/1999 | Leschinsky et al. |
| 5,871,525 A | 2/1999 | Edwards et al. |
| 5,879,366 A | 3/1999 | Shaw et al. |
| 5,888,220 A | 3/1999 | Felt et al. |
| 5,888,223 A | 3/1999 | Bray, Jr. |
| 5,888,224 A | 3/1999 | Beckers et al. |
| 5,891,558 A * | 4/1999 | Bell et al. ..................... 424/425 |
| 5,893,856 A | 4/1999 | Jacob et al. |
| 5,893,890 A | 4/1999 | Pisharodi |
| 5,895,411 A | 4/1999 | Irie |
| 5,897,593 A | 4/1999 | Kohrs et al. |
| 5,904,648 A | 5/1999 | Arndt et al. |
| 5,906,631 A | 5/1999 | Imran |
| 5,908,428 A | 6/1999 | Scirica et al. |
| 5,919,200 A | 7/1999 | Stambaugh et al. |
| 5,941,899 A | 8/1999 | Granger et al. |
| 5,944,738 A | 8/1999 | Amplatz et al. |
| 5,954,636 A | 9/1999 | Schwartz et al. |
| 5,954,766 A | 9/1999 | Zadno-Azizi et al. |
| 5,964,807 A | 10/1999 | Gan et al. |
| 5,972,015 A | 10/1999 | Scribner et al. |
| 5,972,031 A | 10/1999 | Biedermann et al. |
| 5,984,927 A | 11/1999 | Wenstrom, Jr. et al. |
| 5,986,168 A * | 11/1999 | Noishiki ....................... 424/422 |
| 5,989,230 A | 11/1999 | Frassica |
| 6,001,130 A | 12/1999 | Bryan et al. |
| 6,003,517 A | 12/1999 | Sheffield et al. |
| 6,007,563 A | 12/1999 | Nash et al. |
| 6,007,570 A | 12/1999 | Sharkey et al. |
| 6,013,052 A | 1/2000 | Durman et al. |
| 6,016,806 A | 1/2000 | Webb |
| 6,020,380 A | 2/2000 | Killian |
| 6,022,376 A | 2/2000 | Assell et al. |
| 6,027,525 A | 2/2000 | Suh et al. |
| 6,030,442 A | 2/2000 | Kabra et al. |
| 6,033,427 A | 3/2000 | Lee |
| 6,036,720 A | 3/2000 | Abrams et al. |
| 6,048,346 A | 4/2000 | Reiley et al. |
| 6,056,749 A | 5/2000 | Kuslich |
| 6,056,768 A | 5/2000 | Cates et al. |
| 6,066,108 A | 5/2000 | Lundberg |
| 6,066,154 A | 5/2000 | Reiley et al. |

| | | | | | | |
|---|---|---|---|---|---|---|
| 6,071,292 | A | 6/2000 | Makower et al. | 2002/0016583 A1 | 2/2002 | Cragg |
| 6,077,281 | A | 6/2000 | Das | 2002/0022822 A1 | 2/2002 | Cragg et al. |
| 6,077,291 | A | 6/2000 | Das | 2002/0072767 A1 | 6/2002 | Zhu |
| 6,080,182 | A | 6/2000 | Shaw et al. | 2002/0077656 A1 | 6/2002 | Ginn et al. |
| 6,082,362 | A | 7/2000 | Webb | 2002/0077657 A1 | 6/2002 | Ginn et al. |
| 6,086,608 | A | 7/2000 | Ek et al. | 2002/0077658 A1 | 6/2002 | Ginn |
| 6,093,207 | A | 7/2000 | Pisharodi | 2002/0077701 A1 | 6/2002 | Kuslich |
| 6,095,149 | A | 8/2000 | Sharkey et al. | 2002/0082617 A1 | 6/2002 | Nishtala et al. |
| 6,099,567 | A | 8/2000 | Badylak et al. | 2002/0095179 A1 | 7/2002 | Tenerz et al. |
| 6,122,549 | A | 9/2000 | Sharkey et al. | 2002/0112729 A1 | 8/2002 | DeVore et al. |
| 6,126,675 | A | 10/2000 | Shchervinsky et al. | 2002/0183787 A1 | 12/2002 | Wahr et al. |
| 6,126,682 | A | 10/2000 | Sharkey et al. | 2003/0023267 A1 | 1/2003 | Ginn |
| 6,143,004 | A | 11/2000 | Davis et al. | 2003/0033006 A1 | 2/2003 | Phillips et al. |
| 6,146,380 | A | 11/2000 | Racz et al. | 2003/0045893 A1 | 3/2003 | Ginn |
| 6,146,419 | A | 11/2000 | Eaton | 2003/0050665 A1 | 3/2003 | Ginn |
| 6,156,067 | A | 12/2000 | Bryan et al. | 2003/0088271 A1 | 5/2003 | Cragg et al. |
| 6,162,240 | A | 12/2000 | Cates et al. | 2003/0139819 A1 | 7/2003 | Beer et al. |
| 6,174,322 | B1 | 1/2001 | Schneidt | 2003/0144694 A1 | 7/2003 | Chanduszko et al. |
| 6,174,323 | B1 | 1/2001 | Biggs et al. | 2003/0145865 A1 | 8/2003 | Sterman et al. |
| 6,183,518 | B1 | 2/2001 | Ross et al. | 2003/0208232 A1 | 11/2003 | Blaeser et al. |
| 6,197,042 | B1 | 3/2001 | Ginn et al. | 2003/0225421 A1 | 12/2003 | Peavey et al. |
| 6,206,907 | B1 | 3/2001 | Marino et al. | 2004/0019330 A1 | 1/2004 | Ashby |
| 6,206,921 | B1 | 3/2001 | Guagliano et al. | 2004/0059375 A1 | 3/2004 | Ginn et al. |
| 6,206,922 | B1 | 3/2001 | Zdeblick et al. | 2004/0073242 A1 | 4/2004 | Chanduszko |
| 6,206,923 | B1 | 3/2001 | Boyd et al. | 2004/0098042 A1 | 5/2004 | Devellian et al. |
| 6,214,370 | B1 * | 4/2001 | Nelson et al. ............... 424/425 | 2004/0098121 A1 | 5/2004 | Opolski |
| 6,221,109 | B1 | 4/2001 | Geistlich et al. | 2004/0133236 A1 | 7/2004 | Chanduszko |
| 6,231,561 | B1 | 5/2001 | Frazier et al. | 2004/0204654 A1 | 10/2004 | Egnelov et al. |
| 6,240,849 | B1 | 6/2001 | Holler | 2005/0065549 A1 | 3/2005 | Cates et al. |
| 6,241,768 | B1 * | 6/2001 | Agarwal et al. ............... 606/151 | 2005/0085854 A1 | 4/2005 | Ginn |
| 6,248,131 | B1 | 6/2001 | Felt et al. | 2005/0085856 A1 | 4/2005 | Ginn |
| 6,258,100 | B1 | 7/2001 | Alferness et al. | 2005/0192606 A1 | 9/2005 | Paul et al. |
| 6,270,515 | B1 | 8/2001 | Linden et al. | 2005/0267528 A1 | 12/2005 | Ginn |
| 6,287,290 | B1 | 9/2001 | Perkins et al. | | | |
| 6,290,674 | B1 | 9/2001 | Roue et al. | | | |
| 6,293,951 | B1 | 9/2001 | Alferness et al. | | | |

FOREIGN PATENT DOCUMENTS

| | | | |
|---|---|---|---|
| 6,296,657 | B1 | 10/2001 | Brucker |
| 6,302,898 | B1 | 10/2001 | Edwards et al. |
| 6,306,114 | B1 | 10/2001 | Freeman et al. |
| 6,319,263 | B1 | 11/2001 | Levinson |
| 6,327,505 | B1 | 12/2001 | Medhkour et al. |
| 6,346,112 | B2 | 2/2002 | Adams |
| 6,348,064 | B1 | 2/2002 | Kanner |
| 6,350,274 | B1 | 2/2002 | Li |
| 6,368,341 | B1 | 4/2002 | Abrahamson |
| 6,379,368 | B1 | 4/2002 | Corcoran et al. |
| 6,440,452 | B2 * | 8/2002 | Rees et al. ............... 424/422 |
| 6,447,539 | B1 | 9/2002 | Nelson et al. |
| 6,458,100 | B2 | 10/2002 | Roue et al. |
| 6,464,645 | B1 | 10/2002 | Park et al. |
| 6,482,224 | B1 | 11/2002 | Michler et al. |
| 6,482,235 | B1 | 11/2002 | Lambrecht et al. |
| 6,494,848 | B1 | 12/2002 | Sommercorn et al. |
| 6,517,559 | B1 | 2/2003 | O'Connell |
| 6,547,810 | B1 | 4/2003 | Sharkey et al. |
| 6,554,833 | B2 | 4/2003 | Levy et al. |
| 6,626,918 | B1 | 9/2003 | Ginn et al. |
| 6,645,225 | B1 | 11/2003 | Atkinson |
| 6,656,206 | B2 | 12/2003 | Corcoran et al. |
| 6,663,655 | B2 | 12/2003 | Ginn et al. |
| 6,682,489 | B2 | 1/2004 | Tenerz et al. |
| 6,695,867 | B2 | 2/2004 | Ginn et al. |
| 6,699,261 | B1 | 3/2004 | Cates et al. |
| 6,702,835 | B2 | 3/2004 | Ginn |
| 6,716,179 | B2 | 4/2004 | Burbank et al. |
| 6,776,784 | B2 | 8/2004 | Ginn |
| 6,846,319 | B2 | 1/2005 | Ginn et al. |
| 6,860,895 | B1 | 3/2005 | Akerfeldt et al. |
| 7,008,439 | B1 | 3/2006 | Janzen et al. |
| 7,144,411 | B2 | 12/2006 | Ginn et al. |
| 7,317,951 | B2 | 1/2008 | Schneider et al. |
| 7,361,183 | B2 | 4/2008 | Ginn |
| 2001/0003158 | A1 | 6/2001 | Kensey et al. |
| 2001/0037808 | A1 | 11/2001 | Deem et al. |
| 2001/0052344 | A1 | 12/2001 | Doshi |
| 2002/0002386 | A1 | 1/2002 | Ginn et al. |

| | | |
|---|---|---|
| DE | 19710392 | 7/1999 |
| EP | 0432321 A1 | 12/1989 |
| EP | 0647430 | 4/1995 |
| EP | 0700671 | 3/1996 |
| EP | 1033115 | 9/2000 |
| EP | 1078601 | 2/2001 |
| FR | 2639823 | 6/1990 |
| WO | WO 92/05828 | 4/1992 |
| WO | WO 93/08740 | 5/1993 |
| WO | WO 95/05206 | 2/1995 |
| WO | WO 97/26847 | 7/1997 |
| WO | WO 98/02100 | 1/1998 |
| WO | WO 98/19605 A | 5/1998 |
| WO | WO 98/20939 | 5/1998 |
| WO | WO 98/48706 | 11/1998 |
| WO | WO 99/02100 | 1/1999 |
| WO | WO 99/02108 | 1/1999 |
| WO | WO 99/02214 | 1/1999 |
| WO | WO 99/61084 | 12/1999 |
| WO | WO 00/71032 | 1/2000 |
| WO | WO 00/07506 | 2/2000 |
| WO | WO 0062699 | 10/2000 |
| WO | WO 00/69374 | 11/2000 |
| WO | WO 00/71032 | 11/2000 |
| WO | WO 01/02042 | 1/2001 |
| WO | WO 01/10316 | 2/2001 |
| WO | WO 01/13839 | 3/2001 |
| WO | WO 01/13908 | 3/2001 |
| WO | WO 01/21247 | 3/2001 |
| WO | WO 01/26588 | 4/2001 |
| WO | WO 01/28464 | 4/2001 |
| WO | WO 01/45577 | 6/2001 |
| WO | WO 01/45579 | 6/2001 |
| WO | WO 01/60288 | 8/2001 |
| WO | WO 01/66045 | 9/2001 |
| WO | WO 01/66190 | 9/2001 |
| WO | WO 01/87170 | 11/2001 |
| WO | WO 03/047434 A1 | 6/2003 |

* cited by examiner

VASCULAR PLUG HAVING COMPOSITE CONSTRUCTION

RELATED APPLICATION

This patent application is a continuation-in-part of U.S. patent application Ser. No. 10/142,735, filed May 10, 2002, now U.S. Pat. No. 6,896,692, which is a continuation-in-part of U.S. patent application Ser. No. 09/866,548, filed May 25, 2001, now U.S. Pat. No. 6,663,655, which is a continuation-in-part of U.S. patent application Ser. No. 09/738,431, filed Dec. 14, 2000, now U.S. Pat. No. 6,846,319, the disclosures of which are expressly incorporated by reference herein.

FIELD OF THE INVENTION

The present invention relates generally to apparatus and methods for sealing or closing passages through tissue, and more particularly to devices for sealing punctures or other openings communicating with body lumens, such as blood vessels.

BACKGROUND OF THE INVENTION

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

U.S. Pat. No. 6,033,427, issued to Lee, discloses a method and device for sealing internal puncture sites which, in one embodiment, uses a dual lumen bleed back system in which the distal bleed back ports are axially spaced from each other such that when the obturator is in a certain location, there will be bleed back through one of the lumens, but not through the other.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Various methods and means for determining the location of the distal end of a closure device have been proposed, including "bleed back" methodology such as that disclosed in U.S. Pat. No. 4,738,658 issued to Magro et al. However, prior bleed back devices have been constructed such that blood flow out of the patient continues for a longer period of time during deployment of the sealing means than would be desirable.

A further development in bleed back technology is disclosed in published U.S. Patent Application 2004/0019330, in which a control element having an enlarged distal end is used both to control blood flow through the blood vessel puncture and to provide an indication of the position of the distal end of an introducer sheath by withdrawing the enlarged distal end from the lumen of the blood vessel into the puncture in the wall of the blood vessel such that bleed back is, according to this published application, stopped.

Leschinsky U.S. Pat. No. 5,871,501 discloses the use of an anchor on a guide wire to provide an indication of the location of the wall of a blood vessel to assist in the placement of a hemostatic material to block flow of blood out of a puncture in the vessel.

Although these and other methods and devices have been proposed for deploying a plug to prevent blood flow from a puncture in a blood vessel, a need remains for a safe and effective device and method for deploying a plug for this purpose, and for plugs that are more easily deployed and that provide improved prevention of blood flow.

SUMMARY OF INVENTION

The present invention is directed to improved vascular sealing devices used to seal incisions and/or punctured blood vessels, and to methods of using the devices as well. The vascular sealing devices are particularly useful for sealing incisions and punctures that result from catheterization or interventional procedures, such as angioplasty or stenting, although they are not limited to such uses. These incisions and punctures are commonly made to the femoral artery, and the devices described herein are particularly adapted for these purposes. It should be understood, however, that the devices may also be used to seal incisions and/or punctures in other blood vessels or organs.

In several of the preferred embodiments, the sealing device includes a sealing member and a tether. The sealing member generally performs the function of occupying a space in an incision, puncture, or other wound and sealing the space in the incision, puncture, or wound that it occupies, to prevent further blood flow. The tether is typically attached in some manner to the sealing member, and provides the user with the ability to withdraw the sealing member if necessary. In certain embodiments, the tether also provides the user with the ability to manipulate the sealing member for desired effect, such as to radially expand the sealing member within the incision. In a particularly preferred form, the sealing device further includes a restraining member associated with the sealing member. The restraining member provides the ability to more securely restrain the sealing member to prevent it from migrating from the deployment location within a tissue tract. The restraining member may also provide an additional capability of manipulating the sealing member after deployment.

In several preferred embodiments, it is desirable to have the sealing member material expand when the sealing member is deployed and exposed to blood flow from the target vessel. This expansion may cause the sealing member, and therefore the sealing device, to expand radially upon deployment and to thereby engage the incision tissue more firmly, thus tending to prevent migration of the sealing device and increase the effectiveness of the seal.

The sealing device may take any of a variety of different forms or shapes depending upon the nature of the intended use, the material used to make up the device, and other factors. For example, the sealing device may take the form of an undefined mass in situations where the size and/or shape of the sealing device is not a priority or where the sealing portion of the device is restrained by a restraining portion. In another example, the sealing device takes the form of a disc that is adapted to occupy an incision or puncture wound. Other examples include multiple-disc sealing members, and a pair of discs serving as endcaps to a separate tube shaped member. Still further examples include a solid or rolled tube and a mechanical flower. Other and further shapes and sizes are possible, as is any combinations of these shapes and sizes.

Preferably, the tether is attached to the sealing member and is adapted to extend proximally from the sealing member, through and out of the incision, thereby allowing for manipulation by the user. The tether may be used to adjust the sealing member after its deployment, such as by increasing the effective radial dimension of the sealing member, or to remove the sealing member altogether if necessary.

In several preferred embodiments, the sealing device has a composite structure that includes one or more sealing members, as described above, and one or more restraining members. Preferably, the restraining member provides the ability to more easily deliver a sealing member and the ability to reduce the likelihood that the sealing member will migrate after its deployment. In a particular preferred form, the restraining member comprises a braided "sock" that encloses the sealing member and allows the sealing member to be more easily delivered to an incision tract.

In several preferred embodiments, the sealing member, restraining member, and the tether of the vascular sealing device are preferably formed of bioabsorbable materials such as collagen, polyglycolic acids (PGAs), polylactides (PLAs), hydrogel, or gel-foam. These materials may be provided in solid, gel, foam, felt, or other forms. Of these, hydrogels, such as hydroxypropyl cellulose (HPC) hydrogels, are particularly preferred to be used to make the sealing member due to several of their physical properties. In particular, hydrogels are highly absorbent and exhibit high mechanical strength after absorbing a large amount of liquid.

In several alternative embodiments, the sealing device has a composite structure that includes one or more sealing members, as described above, and one or more restraining members. In the alternative embodiments, either the sealing member or the restraining member is formed of a non-bioabsorbable material, while the other member is formed of a bioabsorbable material. Thus, in the alternative embodiments, a bioabsorbable sealing member may be associated with a non-bioabsorbable restraining member, or a non-bioabsorbable sealing member may be associated with a bioabsorbable restraining member. Examples of non-bioabsorbable materials suitable for use in the sealing member or restraining member include nylon, stainless steel, ceramic materials, titanium, gold, platinum, nickel, nickel-titanium alloys, other metals and metal alloys, and other conventional materials suitable for medical use. For example, the restraining member may be formed of a nylon mesh, or of a mesh or braids of stainless steel filaments.

The vascular sealing devices described herein may be deployed by any suitable mechanism. One such mechanism particularly adapted for deploying such devices in an incision created by a catheterization or interventional procedure is described in co-pending U.S. patent application Ser. No. 10/850,795, entitled "Locator and Delivery Device and Method of Use," filed on May 21, 2004, and assigned to Ensure Medical, Inc., the assignee herein. The foregoing application is hereby incorporated by reference in its entirety as if fully set forth herein.

The descriptions herein are particularly directed to sealing puncture wounds created during catheterization or interventional procedures, particularly to such wounds in the femoral artery, but it is to be understood that the vascular sealing devices of the present invention can be used to seal other blood vessels and puncture wounds in them. With that understanding, we turn to a more detailed description of the preferred embodiments.

DETAILED DESCRIPTION OF THE PREFERRED EMBODIMENTS

Figure 1A:
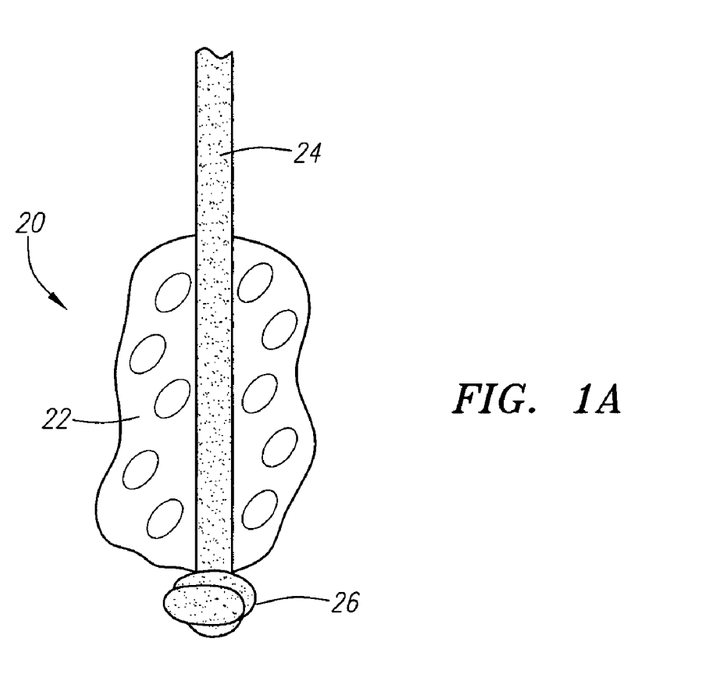
FIG. 1A is an illustration of a vascular sealing device according to the present invention.
Figure 1B:
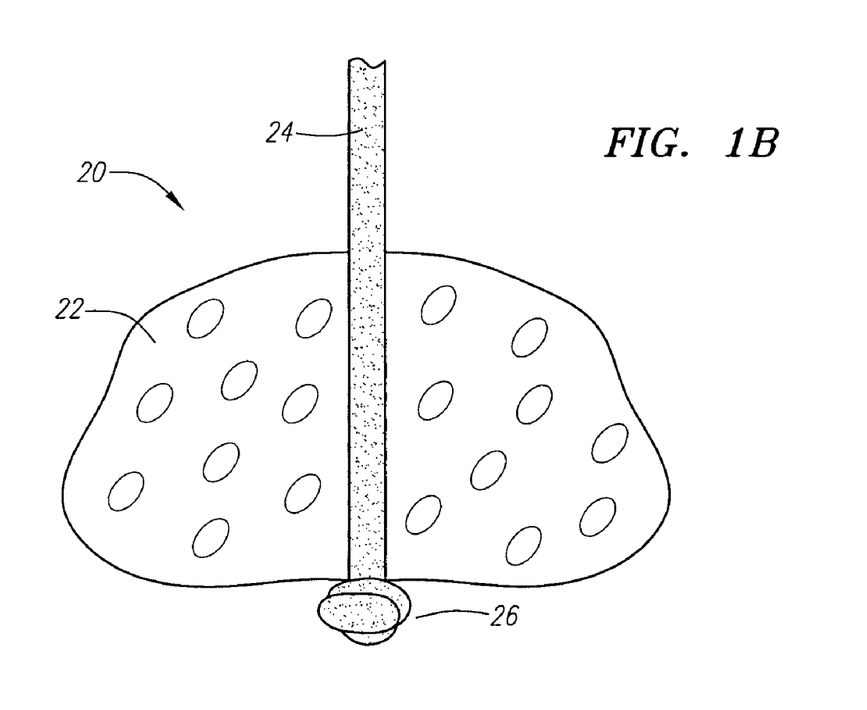
FIG. 1B is an illustration of the device shown in FIG. 1A, shown in an expanded state.

FIGS. 1A and 1B are rudimentary illustrations of a vascular sealing device in accordance with the present invention. The device 20 includes a sealing member 22 retained on a tether 24. The sealing member 22 is preferably retained on the tether 24 at or near its distal end point by a stop member 26 formed at the distal end of the tether 24. The stop member 26 is preferably a knot formed at the distal end of the tether 24.

FIG. 1A shows the device in its unexpanded, predeployment state. FIG. 1B shows the device after it has expanded due to fluid exposure.

The sealing member 22 is formed from a material that is able to expand, or to be expanded, once the sealing device 22 is deployed for use. The sealing member is preferably formed from a bioabsorbable material, but, in several alternative embodiments, the sealing member may be formed from a non-bioabsorbable material. Examples of suitable bioabsorbable materials include bioabsorbable collagen, polyglycolic acids (PGAs), polylactides (PLAs), polyglycol-lactides (PGLAs), hydrogels, and gel-foams. These materials may be provided in solid, gel, foam, felt, or other forms as appropriate for the particular application. Of these materials, hydrogels are particularly preferred due to several of their physical properties. A hydrogel is an absorbent, microporous gel comprising a crosslinked polymer having interconnected fluid cells distributed throughout its mass. Hydrogels absorb fluids very quickly, and exhibit high mechanical strength even after absorbing large amounts of fluids. Moreover, hydrogels typically expand isotropically, meaning that they are able to maintain their original shapes during and after expansion due to fluid absorption. Additional information relating to hydrogels suitable for use in the vascular sealing devices described herein can be found in U.S. Pat. Nos. 5,573,994 and 6,030,442, each of which is incorporated herein by reference in its entirety as if fully set forth herein.

Examples of nonbioabsorbable materials that may be used to form the sealing member 22 include nylon, stainless steel, ceramic materials, titanium, gold, platinum, nickel, nickel-titanium alloys, other metals and metal alloys, and other conventional materials suitable for medical use.

The sealing member 22 of the device shown in FIG. 1A has a generally tubular shape that surrounds the tether 24 near its end. The sealing member 22 may be loosely or firmly secured to the tether 24 by conventional means, or it may be allowed to slide along at least a portion of the length of the tether 24.

The tether 24 shown in the FIG. 1A sealing device performs at least the function of providing the user the ability to retrieve the sealing device 20 from its deployed state if necessary. The tether 24 is preferably formed of conventional suture material, such as a biodegradable polymer having sufficient tensile strength to perform the above functions. Examples of such materials include PGA, PLA, and PGLA polymers. Alternatively, the tether may be formed of a non-bioabsorbable material such as those described above.

The stop member 26 shown in the FIG. 1A sealing device performs at least the function of retaining the sealing member 22 on the tether 24. The stop member 26 may be formed of any biocompatible material suitable to perform this purpose. Alternatively, as in the device 20 shown in FIGS. 1A and 1B, the stop member 26 may comprise a knot formed at the end of the tether 24.

The sealing device 20 is particularly adapted to be used to seal an incision, puncture, or other wound found in the body of a patient, typically a human or other mammal. The device 20 may be delivered to the wound site by any suitable means. For example, in the case of an incision created to gain access to the femoral artery for a catheterization or other interventional procedure, the device may be delivered to the incision tract using the delivery device described in co-pending U.S. patent application Ser. No. 10/850,795, entitled "Locator and Delivery Device and Method of Use," filed on May 21, 2004, and assigned to Ensure Medical, Inc., the assignee herein (hereinafter referred to as "the '795 application"). The delivery device described in the '795 application is adapted to deliver a vascular plug or other sealing device in an incision tract to a point proximal to the blood vessel. In the case of the vascular sealing device 20 shown in FIG. 1A herein, once deployed, the sealing member 22 is exposed to blood flow from the blood vessel. This exposure causes the sealing member 22 to expand due to absorption of the blood, as shown in FIG. 1B. This expansion of the sealing member 22, which has been inserted into the incision tract, causes the sealing member 22 to lodge itself firmly in the incision tract, thereby preventing the sealing device 20 from migrating out of position and creating an effective seal that prevents blood flow from the vessel.

The components making up the sealing device 20 may be formed entirely of bioabsorbable materials, or they may be formed of a combination of bioabsorbable and non-bioabsorbable materials. For example, the sealing member 22 may be formed of one or more bioabsorbable materials, while the tether 24 is formed of a nonbioabsorbable material. Other combinations are also possible.

Optionally, a clotting agent or other hemostasis promoting material—such as a thromboplastin or other conventional clotting agent—may be incorporated into, added to, or used in combination with the sealing device 20.

Figure 2A:
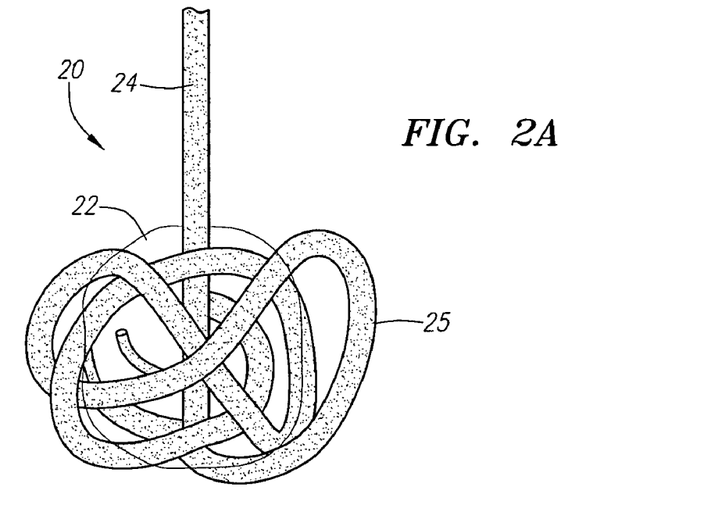
FIG. 2A is an illustration of a vascular sealing device according to an embodiment of the present invention.
Figure 2B:
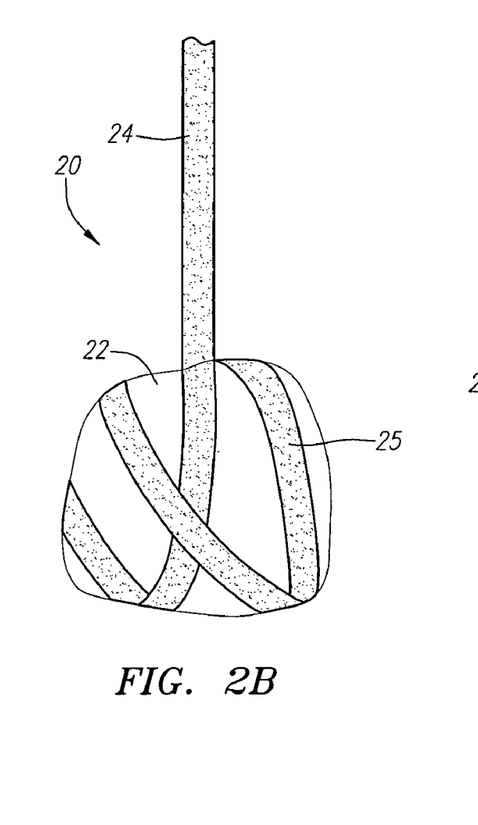
FIG. 2B is an illustration of the device shown in FIG. 2A, shown in an unexpanded state.
Figure 2C:
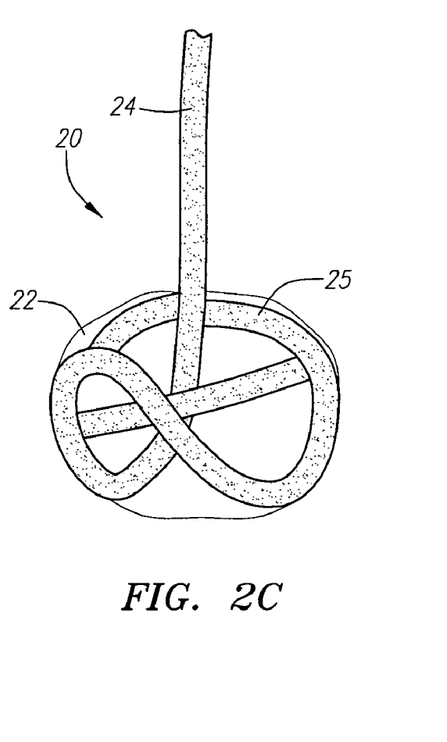
FIG. 2C is an illustration of the device shown in FIG. 2A, shown in an expanded state.

FIGS. 2A through 2C show an alternative embodiment of a vascular sealing device 20 in which the tether 24 is used to enclose and retain the sealing member 22. With reference to FIG. 2A, the device 20 includes a sealing member 22 and a tether 24. The sealing member 22 and tether 24 may be formed of any of the same materials described above in relation to the sealing device 20 shown in FIGS. 1A and 1B. The tether 24 is formed in a surgical knot 25 at its distal end in order to loosely enclose the sealing member 22. In FIG. 2B, the device 20 is shown with the surgical knot 25 snugged in order to more firmly enclose and retain the sealing member 22 prior to deployment of the device. Upon deployment into an incision tract, the sealing member 22 comes into contact with blood flowing from a vessel and expands, providing a seal, as shown in FIG. 2C.

Figure 3A:
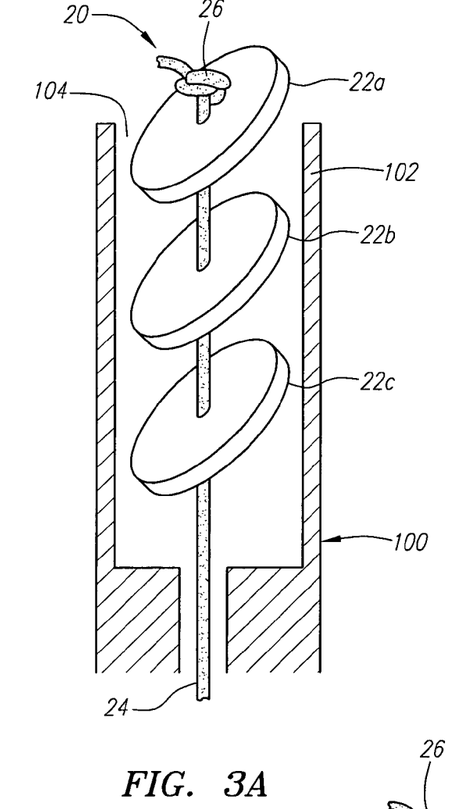
FIG. 3A is an illustration of another vascular sealing device according to the present invention, shown within a delivery tube prior to deployment.
Figure 3B:
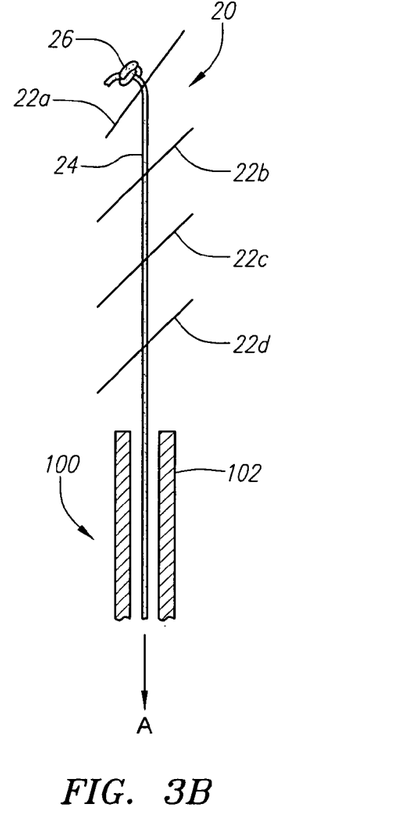
FIG. 3B is an illustration of the vascular sealing device shown in FIG. 3A, shown after deployment by a delivery tube.
Figure 3C:
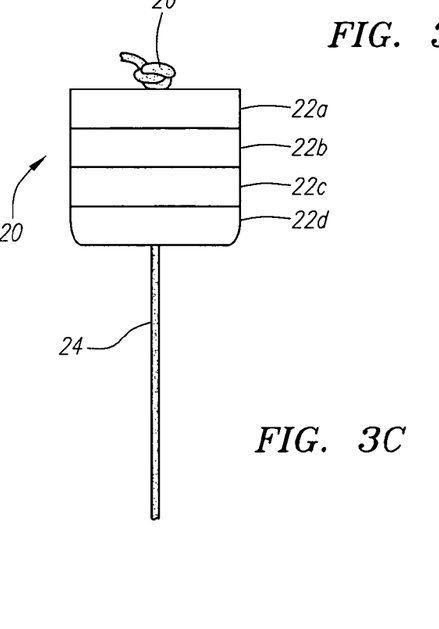
FIG. 3C is an illustration of the vascular sealing device shown in FIG. 3A, shown after alignment and compression of the discs contained on the device.

Turning to FIGS. 3A through 3C, an alternative embodiment of a vascular sealing device 20 includes a number of disc-shaped sealing member 22a-d that are slidably attached to the end of a tether 24. A stop member 26, preferably a knot formed at the distal end of the tether, retains the sealing members 22a-c on the tether 24. The disc-shaped sealing members 22a-d and tether 24 may be formed of any of the same materials described above in relation to the sealing device 20 shown in FIGS. 1A and 1B.

Turning first to FIG. 3A, the sealing device 20 is shown loaded into a delivery device 100, the distal end of which is shown in the Figure. The delivery device has a cylindrical delivery tube 102, shown in cross-section in FIG. 3A, which in turn has an opening 104 at its distal end. The internal space defined by the interior of the delivery tube 102 is adapted to receive and retain the sealing device 20 for delivery to an incision. Once the delivery device 100 is placed into the incision at the appropriate location for delivery of the sealing device 20, the sealing device 20 is deployed through the opening 104 (by a plunger, by retraction of the delivery tube 102, or by another mechanism associated with the delivery device) and into the incision tract, adjacent to the blood vessel opening.

As shown in FIG. 3A, the disc-shaped sealing members 22a-c are spaced apart slightly on the tether 24 in order to be slanted at an angle relative to the axis defined by the tether 24 as they are loaded into and retained within the delivery device. This slanting reduces the radial profile of the disc-shaped sealing members 22a-c, allowing them to be loaded into a smaller diameter delivery tube than would be needed if the sealing members 22a-c were loaded without the slant.

FIG. 3B shows the sealing device 20 after delivery within an incision tract and withdrawal of the delivery device 100. At this point, the sealing members 22a-d remain in the slanted, spaced-apart orientation that they occupied within the interior of the delivery tube 102. Also at this point, the disc-shaped sealing members 22a-d are exposed to blood flow and begin to expand. As shown in FIG. 3C, it is possible and desirable to align and compress the individual disc-shaped sealing members 22a-c by backing the delivery tube 102 up against the most proximally located disc 22d, and pulling on the tether 24 (see arrow "A" in FIG. 3B) to cause the individual discs 22a-d to align and compress against one another while being retained on the tether 24. The effect is to form a radially compressed sealing member 22a-d having an effectively larger radial dimension. The compressed sealing member 22a-d is thereby lodged firmly within the incision tract, seals the tract against blood flow from the blood vessel, and promotes hemostasis.

Figure 4A:
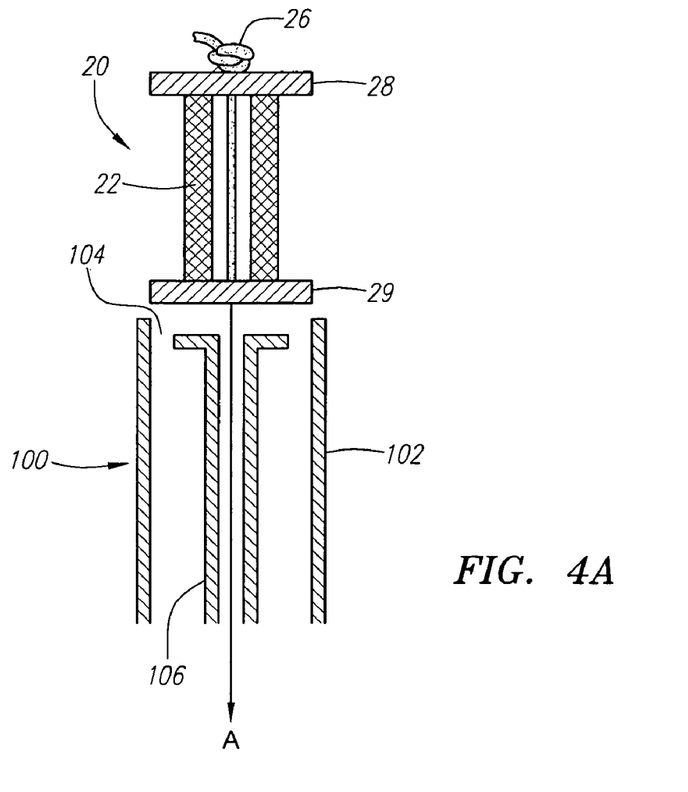
FIG. 4A is an illustration of another vascular sealing device according to the present invention, shown after deployment by a delivery tube.
Figure 4B:
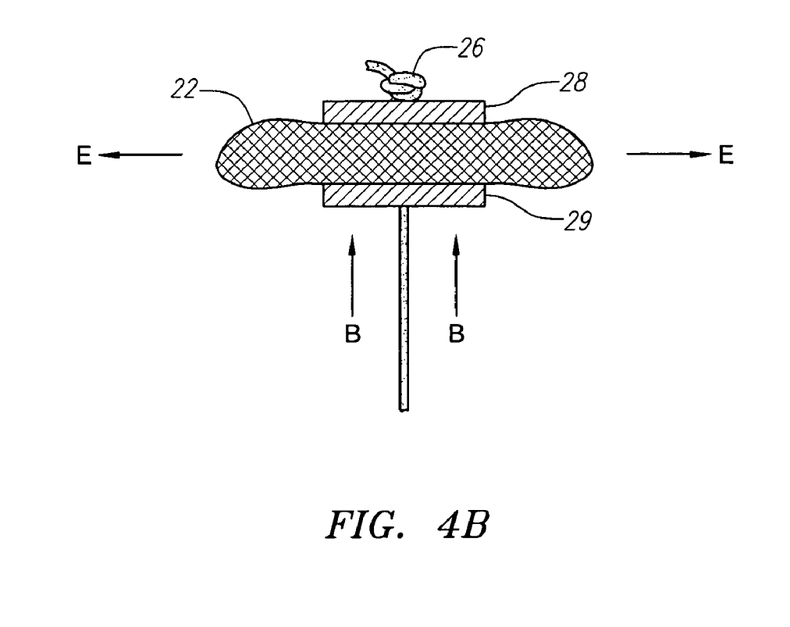
FIG. 4B is an illustration of the vascular sealing device shown in FIG. 4A, shown after compression of the end caps contained on the device.

FIGS. 4A and 4B show still another alternative embodiment of the sealing device 20. In this embodiment, the device includes a sealing member 22 formed as a tube that surrounds a portion of a tether 24. A first endcap 28 is attached to the end of the tether 24, and a second endcap 29 is slidably attached to the tether 24 just proximally of the tubular sealing member 22. The tubular sealing member 22 and tether 24 may be formed of any of the same materials described above in relation to the sealing device 20 shown in FIGS. 1A and 1B. The end caps 28 and 29 are preferably in the form of solid or semi-solid discs. The end caps may be formed of either a bioabsorbable material or a non-bioabsorbable material. In the preferred embodiment, the end caps are formed of a bioabsorbable material, preferably polymeric.

The device 20 shown in FIGS. 4A and 4B may be delivered with a delivery device 100 as shown in FIG. 4A. The device 20 may be expelled from the delivery tube 102 through the opening 104 at its distal end by a plunger 106, or, alternatively, the delivery tube 102 is withdrawn from around the sealing device 20 as the sealing device 20 is retained in place in an incision tract. In either case, the sealing device 20 and delivery device 100 are separated, leaving the sealing device in place within an incision tract.

After delivery, the sealing device 20 may be compressed in a manner similar to that described above in relation to FIGS. 3A through 3C. In reference to FIG. 4B, the plunger 106, the delivery tube 102, or some other member may be placed against the second endcap 29 to provide a back up, and the tether 24 is then drawn taught (see arrow "A") in order to drive the two endcaps 28, 29 toward one another and compress the tubular sealing member 22. Alternatively, the tether 24 may be simply held taut, and the second endcap 29 is then forced down toward the first endcap 28 by the plunger 106, the delivery tube 102, or other member (see arrows "B"), compressing the tubular sealing member 22 in the process. In either event, the end result is that shown in FIG. 4B, with the tubular sealing member 22 compressed radially (see arrows "E") to cause the sealing device to lodge firmly in the incision tract and to provide a seal against blood flow from the blood vessel.

Turning next to FIGS. 5A through 5G, a still further alternative embodiment of the sealing device 20 is shown. In reference to FIG. 5A, the sealing device 20 includes a pair of disc-shaped sealing members 22a-b that are attached to a tether 24 near its distal end. The disc-shaped sealing members 22a-b and tether 24 may be formed of any of the same materials described above in relation to the sealing device 20 shown in FIGS. 1A and 1B. Moreover, although two disc-shaped sealing members 22a-b are shown in the Figures, more or fewer disc-shaped sealing members may be provided.

Figures 5A, 5B, 5C:
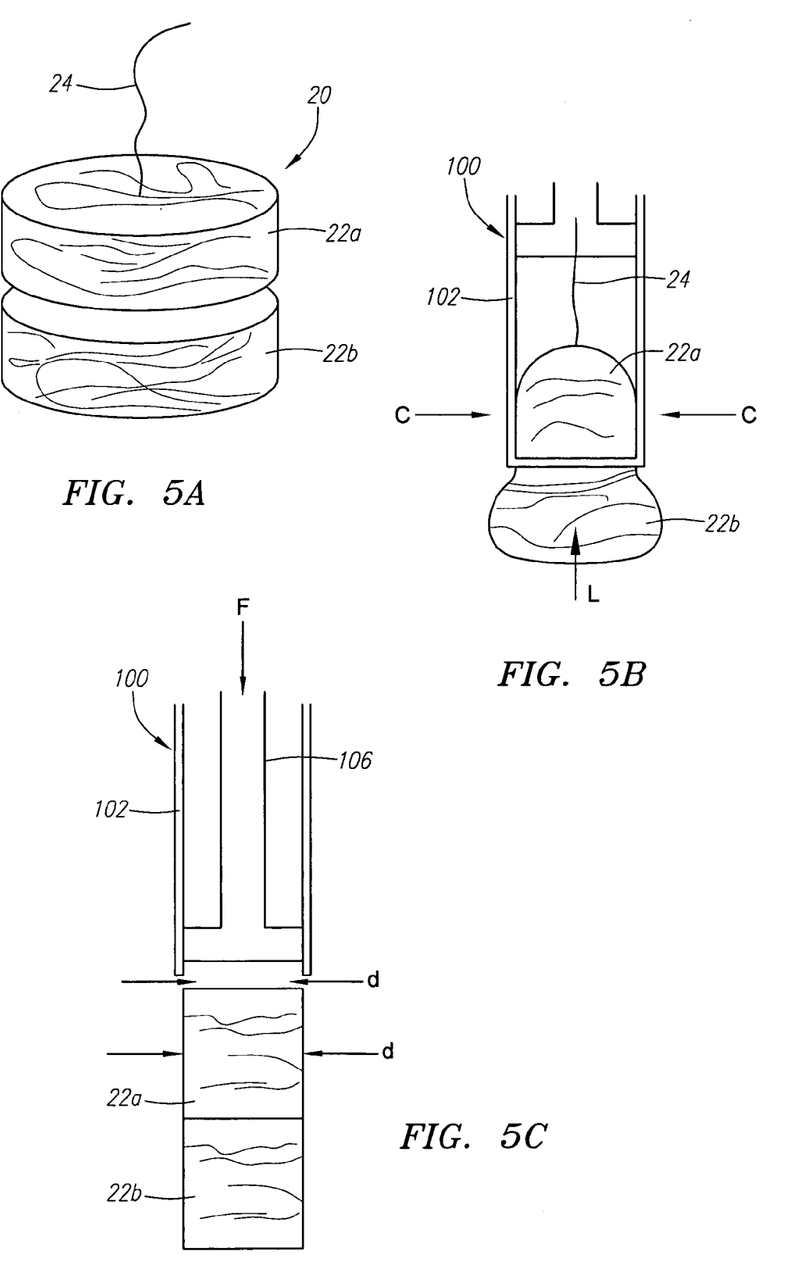
FIG. 5A is an illustration of another vascular sealing device according to the present invention.
FIG. 5B is an illustration of a process for loading the sealing device shown in FIG. 5A into a delivery tube.
FIG. 5C is an illustration of a the sealing device shown in FIG. 5A, shown after deployment from the delivery tube.

As shown in the Figures, the discs are separated by only a small amount of space, unlike the embodiment shown in FIGS. 3A-B. Therefore, as shown in FIG. 5B, in order to load the disc-shaped sealing members 22a-b into the delivery tube 102 of a delivery device 100 (see arrow "L" in FIG. 5B), the disc-shaped sealing members 22a-b are compressed radially during the loading process (see arrows "C" in FIG. 5B). In many cases, one result of this radial compression is that the disc-shaped sealing members 22a-b remain in their compressed state after delivery, i.e., after exiting the delivery tube 102. This effect is illustrated in FIG. 5C, where a plunger 106 associated with the delivery device 100 is shown deploying the sealing device 20 by applying a force (see arrows "F") on the proximal end of the plunger 106. After deployment, the radial dimension (see arrows "d") of the sealing members 22a-b of the sealing device 20 is approximately the same as the inner diameter of the delivery tube 102 (arrows "d"). This effect may be problematic in cases in which the disc-shaped sealing members 22a-b are formed of a material that does not expand significantly upon deployment in an incision tract, and in cases in which the tissue in which the incision tract is formed has become inelastic due to, for example, multiple sheath exchanges during any surgical procedures. In those cases, the sealing member 22a-b will tend to have a radial dimension (effective diameter) that may be slightly smaller than the diameter of the incision, and the tissue surrounding the incision has insufficient elasticity to adequately collapse around the sealing member 22a-b to cause it to firmly lodge in place.

Figure 5D:
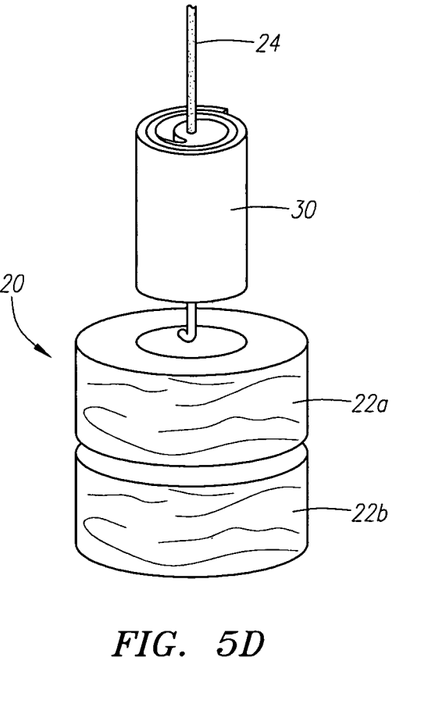
FIG. 5D is an illustration of a process for making another vascular sealing device according to the present invention.
Figure 5E:
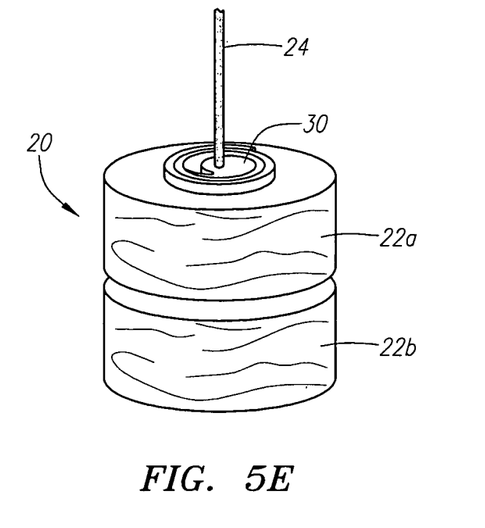
FIG. 5E is an illustration of a vascular sealing device that is the product of the process shown in FIG. 5D.

One solution proposed herein is to provide a volumetric expansion member in association with the sealing member. One example is shown in FIGS. 5D through 5G. Turning to FIG. 5D, each of the pair of disc-shaped sealing members 22a-b is provided with a cylindrical void space at its center. The sealing members 22a-b are preferably formed from a material that demonstrates a relatively small amount of expansion when exposed to fluids in comparison to the expansion capability of the hydrogels described above. An example of a suitable material is a PGA felt material. A separate volumetric expansion member 30 is dimensioned to be inserted into the void space formed in the sealing member 22a-b. As shown in FIG. 5D, the expansion member 30 may be formed as a rolled sheet of highly expandable material, such as a hydrogel foam pad, that is formed to surround the tether 24. The expansion element 30 may then be inserted into the void space formed in the sealing element 22a-b, as shown, for example, in FIG. 5E.

Figure 5F:
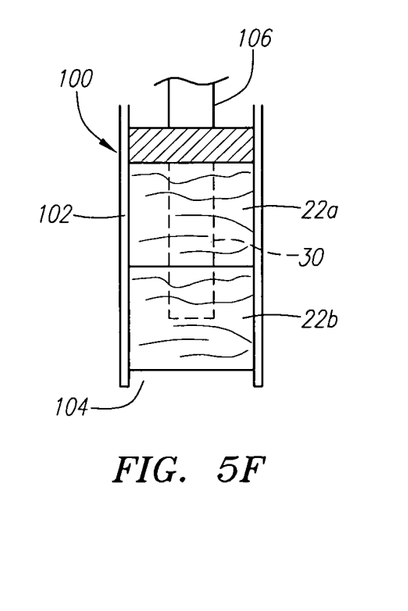
FIG. 5F is an illustration of the vascular sealing device shown in FIG. 5E, shown as loaded into a delivery tube.
Figure 5G:
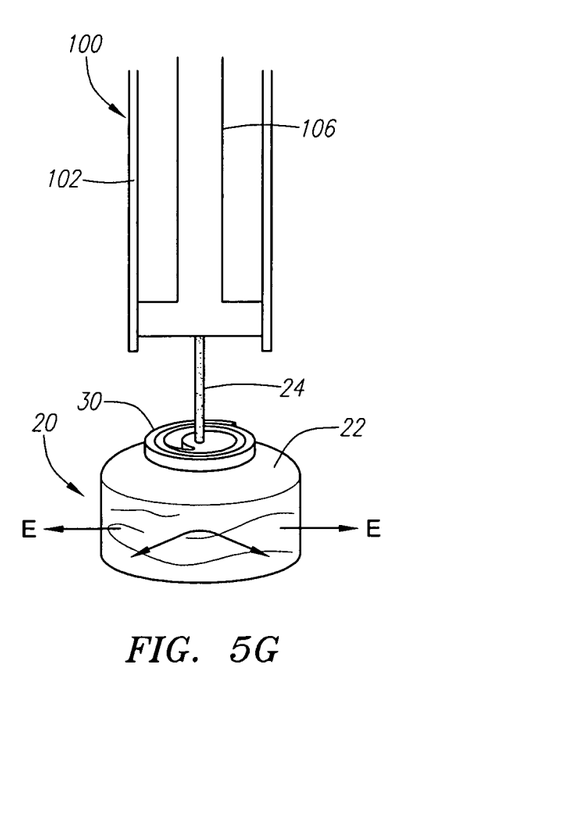
FIG. 5G is an illustration of the vascular sealing device shown in FIG. 5E, shown after deployment from the delivery tube.

The sealing device 20 is then loaded into a delivery device, as shown in FIG. 5F. The delivery device 100, like those described elsewhere herein, includes a delivery tube 102 and a plunger 106 adapted to expel the sealing device 20 through the opening 104 at the distal end of the delivery device 100, or to maintain the position of the sealing device 20 while the delivery tube 102 is withdrawn. Upon deployment, the sealing member 22a-b, including the volumetric expansion member 30, is exposed to blood flow from the blood vessel. Whereas the disc-shaped sealing members 22a-b tend only to expand slightly upon exposure to fluids, the expansion member associated with the sealing member 22a-b expands radially to a much greater degree, as illustrated by arrows "E" in FIG. 5G. This enhances the expansion of the disc-shaped sealing members 22a-b, causing the sealing member 22a-b to more effectively seal the incision tract against further blood flow and to promote hemostasis.

Although a particular orientation of the volumetric expansion member 30 in relation to the sealing member 22a-b is illustrated in FIGS. 5D through 5G, it should be understood that other and different orientations are also possible. For example, the volumetric expansion member may be provided on the exterior of the sealing member, or it may be embedded elsewhere within the sealing member. The expansion member may also take on forms other than a rolled sheet, and the sealing member may take on forms other than the disc-shaped members shown in the Figures. These and other variations are possible while obtaining the advantages provided by a composite structure including one or more sealing members formed from a first material, and one or more volumetric expansion members formed from a second material having substantially greater expansion capacity than the first material. The sealing members and volumetric expansion members may be formed entirely of a combination of bioabsorbable materials, or by a combination of bioabsorbable materials and non-bioabsorbable materials.

Figure 6A:
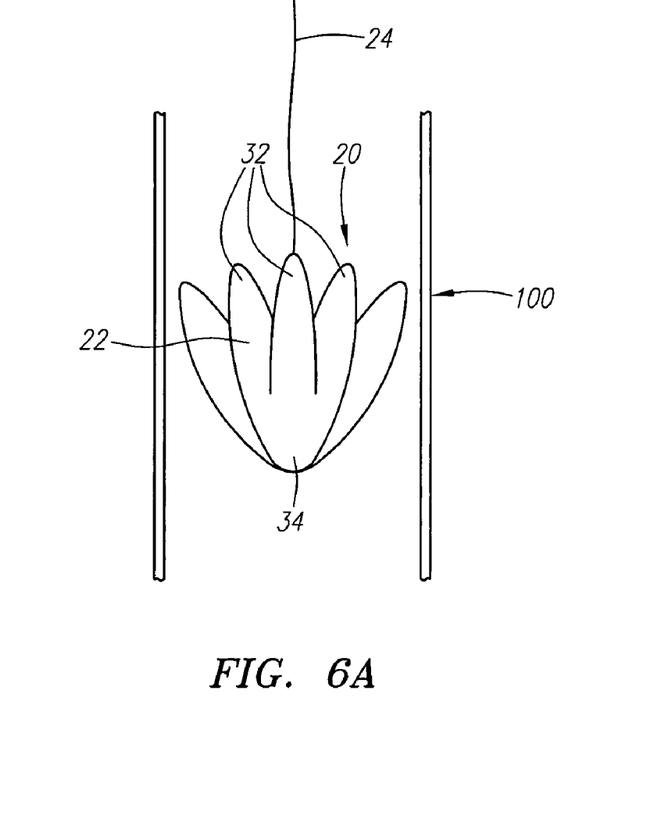
FIG. 6A is an illustration of another vascular sealing device according to the present invention.
Figure 6B:
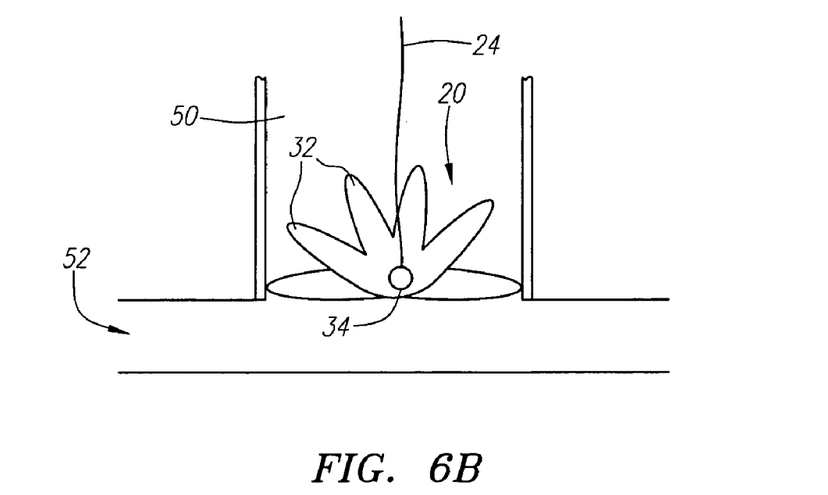
FIG. 6B is an illustration of the device shown in FIG. 6A, shown in an expanded state.

Turning next to FIGS. 6A and 6B, an additional embodiment of a sealing device 20 includes a sealing member 22 in the form of a mechanical flower. The sealing member 22 is preferably formed of a hydrogel or any of the other materials described herein. The mechanical flower includes a number of petals 32 that project radially away from the core 34 of the flower. A tether 24 is attached to the core 34 and is adapted to extend out of an incision upon deployment of the sealing device 20 in an incision tract.

The shape of the mechanical flower is selected due to its capacity for expanding after deployment and exposure to blood flow. For example, as shown in FIG. 6A, prior to deployment (as, for example, while loaded in a delivery device 100), the mechanical flower may be compressed such that all of the petals 34 extend in a single general direction and each is in close proximity the others. Upon deployment, however, the mechanical flower is allowed to "bloom," i.e., to expand such that the petals 34 separate from one another, as shown, for example, in FIG. 6B. This expansion may be caused by a combination of release from the confines of the delivery device and the expansion attributable to the exposure of the superabsorbent sealing member 22 to blood flow in the incision tract 50. This expansion provides the capability for the sealing device to lodge firmly within a tissue tract and to seal the tract against blood flow from the blood vessel 52.

Figure 7A:
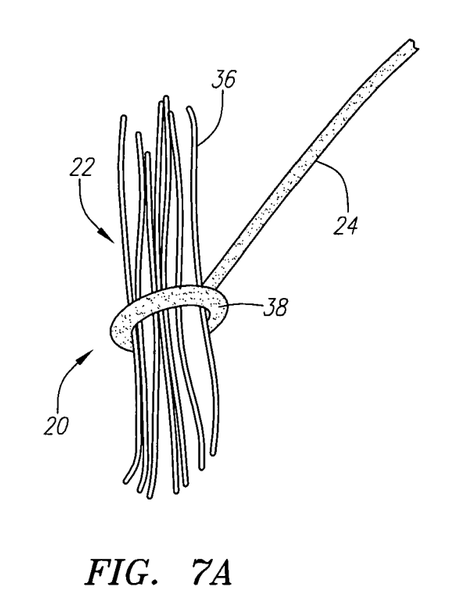
FIG. 7A is an illustration of another vascular sealing device according to the present invention.
Figure 7B:
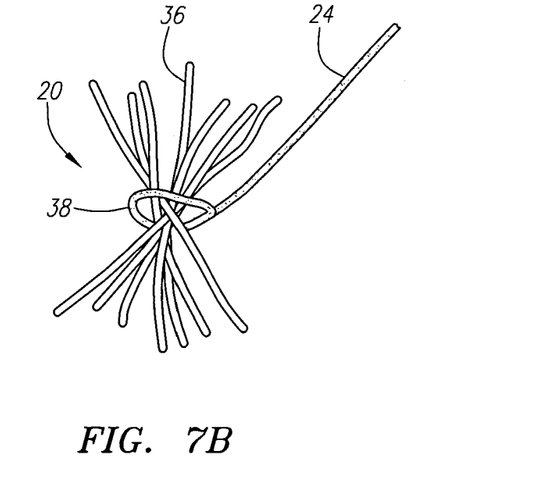
FIG. 7B is an illustration of the device shown in FIG. 7A, shown in an expanded state.

Turning next to FIG. 7, an alternative embodiment of the sealing device 20 includes a collection of individual fibers 36 secured by a center tie 38. The fibers 36 are preferably formed of an hydrogel or other expansive material such as those discussed herein. The center tie 38 is also formed of one of the materials described above, but preferably a more rigid material to provide a secure attachment to the collection of fibers 36 making up the sealing member 22. A tether 24 extends from the center tie 38 and outward from an incision tract once the sealing device 20 is deployed.

A construction of the sealing device that is particularly preferred is a composite construction that includes a tether, a sealing member, and a separate restraining member. One example of this structure is shown in the embodiment illustrated in FIGS. 8A and 8B. In this embodiment, the sealing member 22 preferably comprises a bundle or other body of a material such as a hydrogel or other of those materials discussed herein. The sealing member 22 may be in the form of a felt, a gel, a foam, or other solid or semi-solid material. The sealing member 22 is enclosed and retained by a restraining member 40. In the embodiment shown in FIGS. 8A and 8B, the restraining member 40 comprises a porous basket, such as a knit, braided, or woven fabric that encloses and/or encapsulates the sealing member 22. The restraining member 40 preferably is formed from a material that is porous but fairly rigid and/or that has fairly high tensile strength in order to adequately restrain the sealing member 22. The restraining member may comprise a fairly loose knit, a braided structure, a tightly-woven fabric, or something in between. Preferably, both the sealing member 22 and the restraining member 40 are formed from bioabsorbable materials. In alternative embodiments, however, one of the sealing member 22 and the restraining member 40 is formed of a bioabsorbable material, while the other is formed from a non-bioabsorbable material. Suitable bioabsorbable and non-bioabsorbable materials are those described above.

Figure 8A:
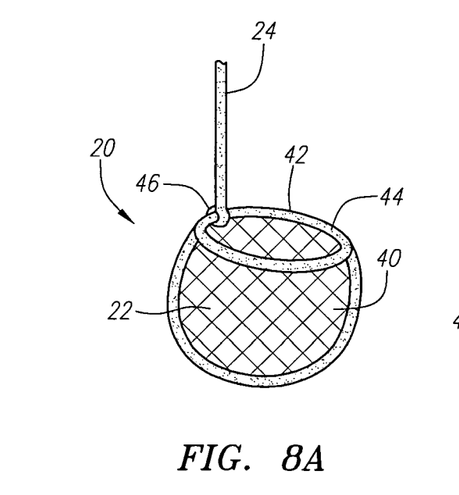
FIG. 8A is an illustration of another vascular sealing device according to the present invention.
Figure 8B:
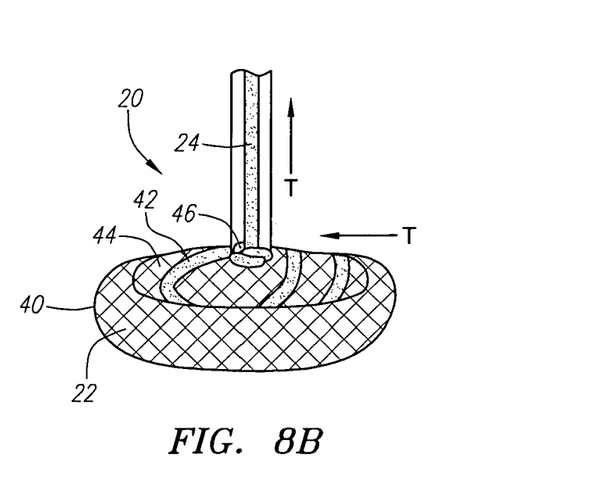
FIG. 8B is an illustration of the vascular sealing device shown in FIG. 8A, shown in an expanded state.

The restraining member 40 shown in FIGS. 8A and 8B includes a mechanism for selectively compressing and radially expanding the sealing member 22 enclosed within the restraining member 40. The mechanism includes a cinch line 42 that runs through a channel 44 formed on the upper periphery of the restraining member 40. A snare knot 46 is formed on the cinch line 42 in the channel 44 and provides the ability to draw the cinch line tight in order to compress the sealing member 22 enclosed in the restraining member 40. When the cinch line 42 is drawn tight (see arrows "T" in FIG. 8B), it changes the shape of the porous basket forming the restraining member 40 by reducing its height, causing the volume of the sealing member 22 enclosed within the restraining member 40 to expand radially, as shown in FIG. 8B. The material making up the restraining member 40 is preferably constructed in such a way to facilitate this change of shape, such as by providing a looser or more flexible braided, woven, or knit structure along the sides of the restraining member 40. The cinch line 42 and snare knot 46 may be accessible by way of the tether 24, or by a separate line that extends from the restraining member 40.

The sealing device 20 shown in FIGS. 8A and 8B may be deployed in a manner similar to those described elsewhere herein. For example, the sealing device 20 may be deployed in an incision tract by using a delivery device having a delivery tube that expels the sealing device 20 from its distal end once properly located within the incision tract. Once deployed, the sealing device 20 will encounter blood flow from the vessel being sealed, thereby causing the sealing member 22 enclosed by the restraining member 40 to expand, including radial expansion. In addition, the user may selectively tighten the cinch line 42 to compress the sealing member 22 to provide additional radial expansion. In this way, the sealing device 20 may be expanded to firmly lodge the device within the incision tract to prevent its migration out of the tract and to seal the tract against blood flow.

Turning to FIGS. 9A through 9I, an additional embodiment of a sealing device is shown, as is a method of making the sealing device. The sealing device shown in FIGS. 9A through 9I is constructed to include a tether, a sealing member, and a restraining member.

Figure 9A:
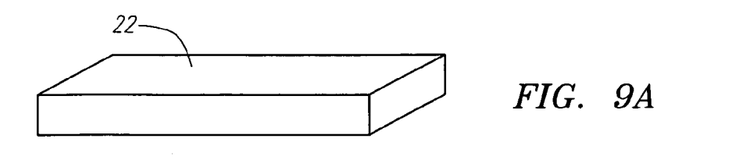
FIG. 9A is an illustration of a pad used as a starting material for a sealing member.
Figure 9B:
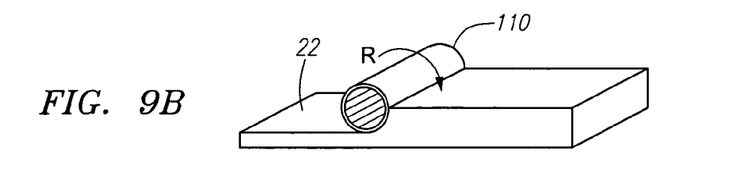
FIG. 9B is an illustration of a process for compressing the pad shown in FIG. 9B.

Turning first to FIG. 9A, in the preferred embodiment the sealing member 22 is a hydrogel foam pad, although other bioabsorbable, highly-expandable materials may be used as well. In other embodiments, the sealing member 22 may be formed from a non-bioabsorbable material. The foam pad preferably has dimensions that allow it to be compressed and rolled (as described below) to a shape and size suitable for receipt in a delivery device and for its ultimate use as a sealing device in an incision tract. In order to optimize the volume and capacity of the sealing member 22, it is preferable to compress the foam pad prior to installation in the sealing device. One method of performing this compression step is to use a compressive roller 110 to apply a compressing force to the pad, much like a rolling pin. This method is illustrated by arrow "R" in FIG. 9B. The result of the compression step is to obtain a highly compressed, flat foam pad of hydrogel or other bioabsorbable (or non-bioabsorbable) material.

Figure 9C:
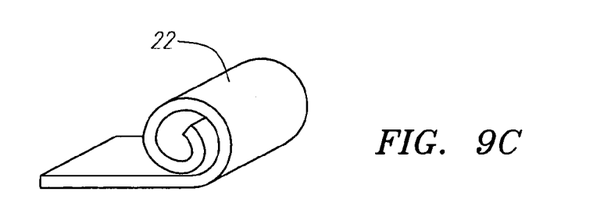
FIG. 9C is an illustration the pad shown in FIG. 9A, after compression, shown partially rolled into a coiled form.

Turning to FIG. 9C, in the preferred embodiment, the sealing member is rolled into a coil. The coil shape is preferred because it creates a low-profile sealing member in the dry state that is capable of a high degree of radial expansion when the sealing member is exposed to blood flow. The low profile in the dry state is useful to facilitate delivery of the sealing device, while the high degree of radial expansion when exposed to fluid is useful to facilitate firmly lodging the sealing device in an incision tract and sealing the tract against blood flow. Other and different shapes and dimensions are also possible, and each may contribute more or less to these objectives. For example, the sealing member may be a wadded or otherwise compressed mass. The coiled sheet shape is a preferred embodiment.

Figure 9D:
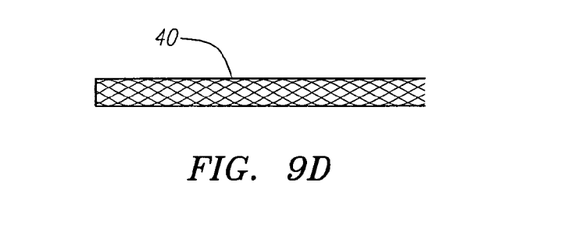
FIG. 9D is an illustration of a tube of braided material suitable for use as a restraining member according to the present invention.

FIG. 9D shows a preferred restraining member 40 for use with the sealing device. The restraining member 40 is a porous, tubular member formed of a knit, woven, or braided material. The composition of the tubular restraining member 40 is preferably of a bioabsorbable material, such as suture material formed from PGA, PLA, or PGLA. In alternative embodiments, the restraining member 40 may be formed of a non-bioabsorbable material, such as nylon or stainless steel filament mesh. The knit or braided structure allows the restraining member 40 to expand when needed to accommodate the sealing member 22 within its interior.

Figure 9E:
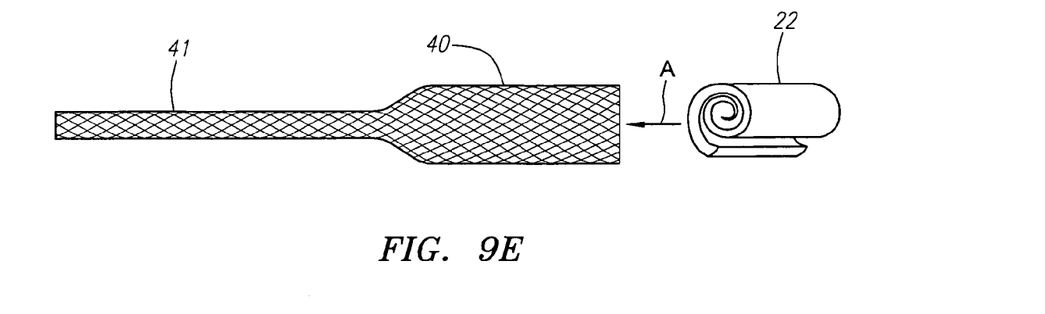
FIG. 9E is an illustration of part of a process of inserting the pad shown in FIG. 9A in its coiled form into the tube shown in FIG. 9D.
Figure 9F:
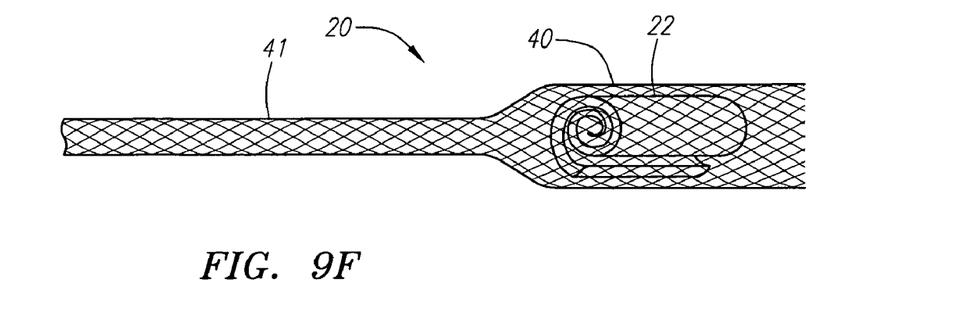
FIG. 9F is an illustration of a vascular sealing device according to the present invention.
Figure 9G:
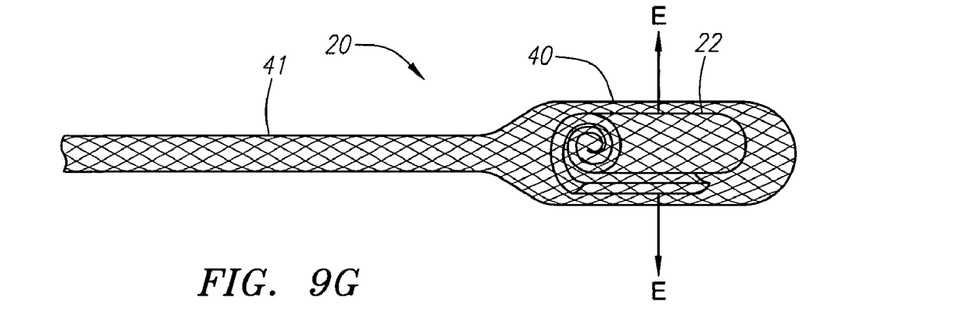
FIG. 9G is an illustration of the device shown in FIG. 9F, shown in an expanded state.

FIG. 9E provides an illustration of a process for inserting the sealing member 22, in this case a compressed and coiled sheet of hydrogel material, into the restraining member 40. The arrow "A" indicates passage of the sealing member 22 into the interior space defined by the restraining member 40, within which the sealing member is enclosed and retained. As shown in the Figure, the woven, braided, or knit structure of the restraining member 40 material allows for expansion of the restraining member 40 to accommodate the sealing member 22. After inserting the sealing member 22 into the restraining member 40, the open end of the restraining member 40 (through which the sealing member has passed) may be closed or sealed to fully enclose the sealing member 22, as shown in FIG. 9F. In addition, a proximal portion 41 of the restraining member 40 that extends proximally of the sealing member 22 may be used instead of, or as a replacement for, a tether as used in other embodiments described herein. Thus, after deployment of the sealing device 20, the proximal portion 41 of the restraining member 40 would extend out of the incision tract and may be used to manipulate the sealing device 20 and/or to remove the sealing device 20 from the incision if necessary.

FIG. 9F illustrates one embodiment of the complete sealing device 20 in its predeployment, unexpanded state. This state, in which the sealing device 20 has a reduced profile, is suitable for loading the device 20 into an appropriate delivery device, such as the delivery devices described previously herein. The sealing device is then able to be delivered by, for example, expelling the device out of the open distal end of a delivery tube, into an incision tract and near an opening in a target blood vessel. Upon exposure to blood flow, the sealing member 22 within the sealing device will expand, as illustrated by the arrows "E" in FIG. 9G. This expansion will cause the sealing device 20 to lodge firmly within the incision tract, sealing the incision against blood flow.

Figure 9H:
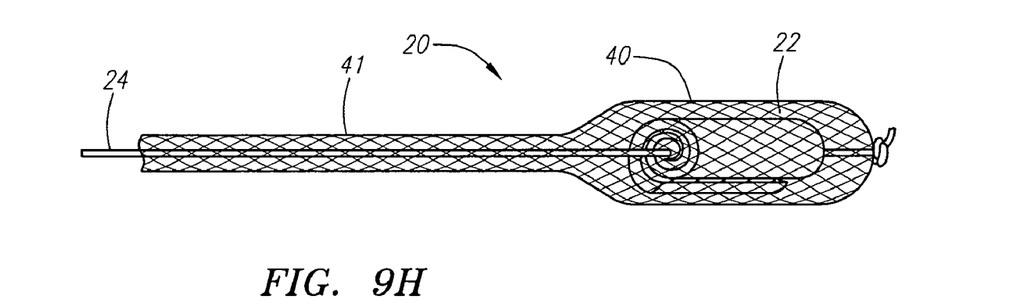
FIG. 9H is an illustration of a vascular sealing device similar to that shown in FIG. 9F, further including a separate tether member.
Figure 9I:
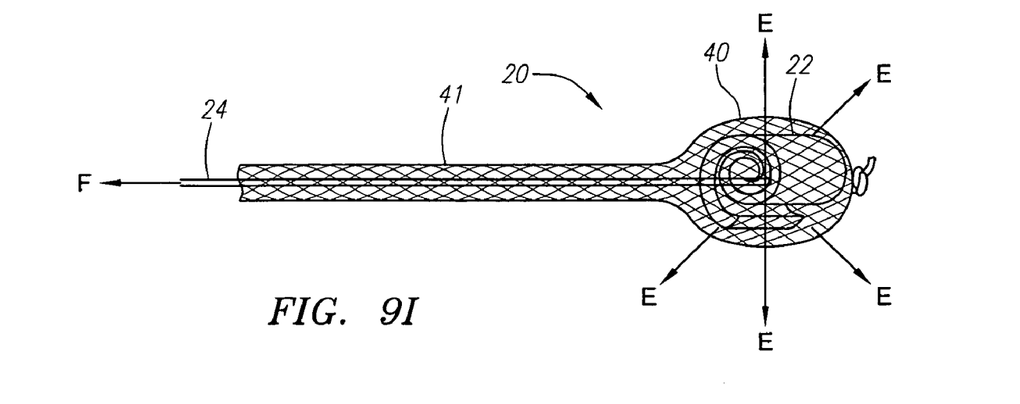
FIG. 9I is an illustration of the device shown in FIG. 9H, shown in an expanded state.

FIGS. 9H and 9I show a sealing device 20 similar to that described above in relation to FIGS. 9F and 9G, but also including a tether 24. The tether 24 is preferably attached to the sealing member 22 and the restraining member 40, and may be used to manipulate the sealing device 20 after deployment, or to remove the sealing device 20 from the incision if necessary. For example, as shown in FIG. 9I, the tether 24 may be attached to the sealing member 22 and restraining member 40 in a manner that allows the user to exert an upward force (see arrows "F") on the tether that increases the radial expansion (arrows "E") of the sealing member 22 inside the restraining member 40. This increased radial expansion due to mechanical manipulation of the sealing device will increase the ability of the device to lodge firmly within the incision tract, seal the incision against blood flow, and promote hemostasis.

As noted above, the several embodiments of the sealing device described herein are preferably constructed of components formed entirely from bioabsorbable materials. However, each of the foregoing embodiments may also be constructed of a combination of one or more components formed from bioabsorbable materials, and one or more components formed from non-bioabsorbable materials.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A device for substantially sealing a wound that extends through tissue to an opening in a body lumen comprising: a restraining member comprising a first bioabsorbable material and defining an interior space therein, a sealing member comprising a second bioabsorbable material at least partially located within the interior space of said restraining member, and an elongated tubular member, wherein the restraining member and the sealing member are releasably disposed in an unexpanded state within the elongated tubular member, and wherein at least the sealing member will expand when placed in the body lumen.

2. The device of claim 1 further comprising a tether attached at a first end to said sealing member.

3. The device of claim 1, wherein said first bioabsorbable material is the same as said second bioabsorbable material.

4. The device of claim 1, wherein said first bioabsorbable material is selected from the group consisting of polyglycolic acid, polylactide, polyglycol-lactide acid, collagen, and hydrogel.

5. The device of claim 1, wherein said restraining member comprises a porous member.

6. The device of claim 5, wherein said restraining member comprises a material having a knit, braided or woven construction.

7. The device of claim 5, wherein said restraining member is a tubular fabric member and said sealing member is a coiled foam pad enclosed by said tubular fabric member.

8. The device of claim 7, wherein said coiled form pad comprises a hydrogel.

9. A method for substantially sealing a wound that extends through tissue to an opening in a body lumen, comprising: providing a sealing device comprising a hydrogel material, at least partially located within an interior space of a restraining member and deploying the sealing device in the wound through an elongated tubular member, wherein the sealing device is releasably disposed in an unexpanded state in the elongated tubular member and wherein at the sealing device will expand when placed in the body lumen, and wherein the restraining member comprises a bioabsorbable material.

10. The method of claim 9, wherein said sealing device further comprises a tether attached at a first end to said sealing device.

11. The method of claim 9, wherein said bioabsorbable material is selected from the group consisting of polyglycolic acid, polylactide, polyglycol-lactide acid, collagen, and hydrogel.

12. The method of claim 9, wherein said restraining member comprises a material having a knit, braided or woven construction.

13. The method of claim 12, wherein said restraining member is a tubular fabric member and said sealing member is a coiled foam pad enclosed by said tubular fabric member.

14. A device for substantially sealing a wound that extends through tissue to an opening in a body lumen comprising: a sealing member, at least a portion of which having a first radial dimension for delivery of said sealing member into the wound and will expand to a second radial dimension upon delivery into said wound and exposure to fluid flow associated with said wound, the second radial dimension being larger than the first radial dimension, and wherein said sealing member comprises a hydrogel, further comprising a restraining member comprising a first bioabsorbable material and defining an interior space therein, said sealing member being located at least partially within the interior space of said restraining member and an elongated tubular member, wherein the sealing device is releasably disposed in a state with the first radial dimension within the elongated tubular member and wherein at least the sealing member will expand to the second radial dimension when placed in the body lumen.

15. The device of claim 14, further comprising a tether connected to said sealing member and having a length sufficient to extend externally of said wound after delivery of the sealing member.

16. The device of claim 15, further comprising a stop member at a terminal end of said tether, said stop device adapted to retain the sealing member on the tether.

17. The device of claim 14, wherein said first bioabsorbable material is selected from the group consisting of polyglycolic acid, polylactide, polyglycollactide acid, collagen, and hydrogel.

* * * * *